United States Patent [19]

Edwards et al.

[11] Patent Number: 4,952,707

[45] Date of Patent: Aug. 28, 1990

[54] ENZYMATICALLY-CLEAVABLE CHEMILUMINESCENT FUSED POLYCYCLIC RING-CONTAINING 1,2-DIOXETANES

[75] Inventors: Brooks Edwards, Cambridge; Irena Y. Bronstein, Newton; Alison A. Laird, Methuen; John C. Voyta, North Reading, all of Mass.

[73] Assignee: Tropix, Inc., Bedford, Mass.

[21] Appl. No.: 213,672

[22] Filed: Jun. 30, 1988

[51] Int. Cl.$^5$ .................... C07D 321/00; C07F 9/655
[52] U.S. Cl. ........................................ 549/221; 435/4; 435/5; 435/7; 436/172; 436/517; 436/537; 536/4.1; 536/18.1; 544/6; 544/35; 544/57; 544/70; 544/102; 544/230; 544/244; 544/264; 546/15; 546/23; 546/88; 546/102; 546/108; 546/121; 546/122; 546/139; 546/152; 546/270; 548/113; 548/119; 548/125; 548/147; 548/152; 548/216; 548/217; 548/260; 548/327; 548/336; 549/17; 549/43; 549/58; 549/223; 549/225; 549/226; 549/227; 549/332; 549/359; 549/378; 549/388; 549/398; 549/462; 549/510; 549/511; 568/328; 568/632; 568/634; 568/737
[58] Field of Search ............... 549/221, 510, 511, 332, 549/17, 43, 58, 223, 225, 226, 227, 359, 378, 388, 395, 462; 536/4.1, 18.1; 544/6, 35, 57, 70, 102, 230, 244, 265; 546/15, 23, 88, 102, 108, 121, 127, 139, 152, 270; 548/113, 119, 125, 147, 152, 216, 217, 260, 327, 336

[56] References Cited

FOREIGN PATENT DOCUMENTS 254051 1/1988 European Pat. Off. .

OTHER PUBLICATIONS

Schaap et al., Tetrahedron Letters, vol. 28, No. 11, 1155-1158 (1987).

Primary Examiner—Richard L. Raymond
Attorney, Agent, or Firm—Lyon & Lyon

[57] ABSTRACT

Chemiluminescent 1,2-dioxetane compounds are disclosed in which the molecule is stabilized at the 3-position on the dioxetane ring against decomposition prior to the molecule's coming in contact with a labile group-removing substance (e.g., an enzyme that will cleave the labile group to cause the molecule to decompose to form at least one light-emitting fluorophore) and substituted at the 4-position on the dioxetane ring with a fused polycyclic ring-containing fluorophore moiety bearing a labile ring substituent whose point of attachment to the fused polycyclic ring, in relation to this ring's point(s) of attachment to the dioxetane ring, is such that the total number of ring atoms separating these points of attachment, including the ring atoms at the points of attachment, is an odd whole number. These odd pattern substituted compounds decompose to emit light of greater intensity and of a different wavelength than that emitted by the corresponding even pattern substituted isomers. They are useful in detecting the presence or determining the concentration of chemical or biological substances in immunoassays, chemical assays and nucleic acid probe assays, and in chemical/physical probe procedures for studying the microstructures of macromolecules. Two or more of them can also be used in combination, or one or more of them can be used together with other chemiluminescent compounds, in multi-channel assays to detect two or more different analytes simultaneously. Novel intermediates used in the preparation of these odd pattern substituted compounds are also disclosed.

18 Claims, No Drawings

ENZYMATICALLY-CLEAVABLE CHEMILUMINESCENT FUSED POLYCYCLIC RING-CONTAINING 1,2-DIOXETANES

FIELD OF THE INVENTION

This invention relates to improved chemiluminescent 1,2-dioxetane compounds and novel intermediates used in their preparation. More particularly, this invention relates to improved chemiluminescent 1,2-dioxetane compounds that contain labile groups removable enzymatically, to produce fluorophores that in turn emit optically detectable energy, usually luminescence in the form of visible light, and that also contain stabilizing groups that prevent these dioxetanes from decomposing before the labile group comes in contact with the substance(s) that will remove it. This invention further relates to the incorporation of such light-emitting reactants in art-recognized immunoassays, chemical assays and nucleic acid probe assays, and to their use as direct chemical/physical probes, to permit an analyte, a chemical or biological substance whose presence, amount or structure is being determined, to be identified or quantified.

BACKGROUND OF THE INVENTION

Chemiluminescent 1,2-dioxetanes and their use in previously-developed chemical and biochemical assays has assumed increasing importance in recent years, particularly with the advent of enzymatically-cleavable 1,2-dioxetanes; see, for example, copending Bronstein U.S. patent application Ser. No. 889,823, "Method of Detecting a Substance Using Enzymatically-Induced Decomposition of Dioxetanes", filed July 24, 1986; Bronstein et al U.S. patent application Ser. No. 140,035, "Dioxetanes for Use in Assays", filed Dec. 31, 1987; Edwards U.S. patent application Ser. No. 140,197, "Synthesis of 1,2-Dioxetanes and Intermediates Therefor", filed Dec. 31, 1987, now abandoned, and Voyta et al U.S. patent application Ser. No. 203,263, "Chemiluminescence Enhancement", filed June 1, 1988.

It is known that chemiluminescent 1,2-dioxetanes substituted at the 4-position on the dioxetane ring with a monocyclic aromatic ring-containing fluorophore moiety can be configured to maximize their charge transfer characteristics ("emission efficiencies") in the excited state and, as a result, increase the intensity of the light emitted when such compounds decompose. This is the so-called "meta effect" discussed in Schaap et al, *Tetrahedron Letters*. p. 1155 (1987). The meta effect, as the name implies, is achieved by placing a labile substituent containing a bond cleavable to yield an electron-rich fluorophore moiety meta to the point of attachment of the monocyclic aromatic ring to the dioxetane ring.

Knowledge of the meta effect, however, would not have enabled those skilled in the art to predict with assurance what effect, if any, substituent placement might have on the intensity of light emitted by the decomposition of chemiluminescent 1,2-dioxetanes substituted at the 4-position on the dioxetane ring with fused polycyclic, rather than monocyclic, ring-containing fluorophore moieties, and certainly would give no guidance whatsoever regarding the duration or the nature, i.e., the wavelength or color, of light emitted by such polycyclic moieties on decomposition.

SUMMARY OF THE INVENTION

This invention is concerned with chemiluminescent 1,2-dioxetanes substituted with certain fused polycyclic ring-containing fluorophore moieties. In particular, it is concerned with chemiluminescent 1,2-dioxetanes stabilized at the 3-position on the dioxetane ring against decomposition prior to the molecule's coming in contact with a labile group-removing substance (i.e., an enzyme that will result in enzymatic cleavage of the dioxetane molecule) and substituted at the 4-position on the dioxetane ring with a fused polycyclic ring-containing fluorophore moiety which is itself substituted in a particular fashion with a labile ring substituent containing a bond which, when cleaved, renders this fluorophore moiety electron-rich and hence renders the dioxetane decomposable to emit light.

It has now been discovered, quite unexpectedly, that if such fused polycyclic ring-containing fluorophore moieties are substituted in a particular pattern, i.e., if they contain at a particular ring position in relation to the polycyclic ring's point(s) of attachment to the dioxetane ring a labile ring substituent having an enzymatically cleavable bond they will, by virtue of this substitution pattern, decompose to emit light of unexpectedly greater intensity in certain environments, as well as light of longer duration, than that emitted by corresponding isomeric compounds, i.e., otherwise identical fused polycyclic ring-substituted 1,2-dioxetanes having the same labile ring substituents on the polycyclic ring but on different ring positions and thus in different substitution pattern.

In contrast to other chemiluminescent materials—for example acridinium esters, or luminols under most conditions—the enzymatically cleavable chemiluminescent 1,2-dioxetanes of this invention, when decomposed, emit light as a glow rather than a flash. The kinetic difference between these two types of light emission is illustrated by Knox Van Dyke, "Bioluminescence and Chemiluminescence: Instruments and Applications" (Boca Raton, Fla.: CRC Press 1985), Vol. 1, p. 5.

High intensity light emission permits the use of simple photodetectors (silicon photodiodes or photographic film, for example) as well as conventionally employed photomultiplier tubes to detect the emitted light. The stability of the emission signal produced by these enhanced intensity chemiluminescent 1,2-dioxetanes also simplifies assay procedures in which they are used as the means by which the analyte is identified or quantified because the chemiluminescent reaction can be initiated prior to transferring the assay mixture to the light detector. Hence, precisely timed operations are not required.

This invention's substitution pattern is one in which the enzymatically cleavable labile ring substituent's point of attachment to the fused polycyclic ring, in relation to this ring's point of attachment to the dioxetane ring, is such that the total number of ring atoms, e.g., ring carbon atoms, separating these two points of attachment, including the carbon atoms at the points of attachment, is an odd whole number. Preferably, the total number of ring atoms separating these two points of attachment, including the ring atoms at the points of attachment, will be an odd whole number of 5 or greater. A naphthalene residue attached by a single bond or through a spiro linkage to the dioxetane ring at this residue's 2-carbon atom and bearing an enzyme-cleavable substituent, e.g., a phosphate ester group, at its 5- or 7-carbon atom, or a naphthalene residue attached at its 1-carbon atom and substituted at its 8-carbon atom, with an enzyme-cleavable substituent are typical examples from among this invention's contemplated odd pattern fused polycyclic aromatic hydrocarbon ring-containing fluorophore moieties.

Most unexpectedly, the novel odd pattern substituted fused polycyclic ring-containing 1,2-dioxetanes of this invention also exhibit on decomposition a pronounced shift in the wavelength of the light emitted, i.e., this light is a different color from that emitted by corresponding isomeric compounds which have an even rather than an odd numbered substitution pattern.

This invention is further concerned with the use of these improved chemiluminescent 1,2-dioxetanes in art-recognized immunoassays, chemical assays and nucleic acid probe assays to detect the presence or determine the concentration of chemical or biological substances, and as direct chemical/physical probes for studying the molecular structures or microstructures of various macromolecules: synthetic polymers, proteins, nucleic acids and the like.

Also, by using either two or more of the improved chemiluminescent 1,2-dioxetanes of this invention, each of which upon decomposition emits light of a different wavelength, or one or more of these compounds together with a different chemiluminescent compound, such as one of the enzymatically decomposable 1,2-dioxetanes disclosed in the aforementioned copending Bronstein, Bronstein et al and Edwards applications, or a chemically or electrochemically cleavable analog thereof, which emits light of yet another wavelength, each of such compounds being structured so as to be decomposable by a different means (e.g., one of a pair of such compounds can contain a phosphate ester group cleavable by a phosphatase and the other an α-D- or β-D-glucoside group cleavable by β-glucosidase, or one such compound as disclosed herein can contain an enzyme-cleavable group and the other a chemically cleavable group such as a hydroxyl group, an alkanoyl or aroyl ester group, or an alkyl or aryl silyloxy group), a multi-channel assay can be designed in which different cleaving means attached to or associated with two or more different analytes will, by cleaving different cleavable dioxetane substituents, induce the emission of light of a different wavelength for each analyte being assayed.

It is, therefore, an object of this invention to provide improved enzymatically cleavable chemiluminescent 1,2-dioxetane compounds and novel intermediates used in preparing them.

A further object of this invention is to provide enzymatically cleavable chemiluminescent 1,2-dioxetanes stabilized at the 3-position on the dioxetane ring against decomposition prior to the molecule's being brought into contact with an enzyme to intentionally cleave an enzymatically cleavable labile substituent's bond, and substituted at the 4-position on the dioxetane ring with a fused polycyclic ring-containing fluorophore moiety which is itself substituted with a labile ring substituent containing a bond which, when cleaved, by an enzyme renders this fluorophore moiety electron-rich and hence renders the dioxetane decomposable to emit light, this labile ring substituent's point of attachment to the fused polycyclic ring, in relation to this ring's point of attachment to the dioxetane ring, being such that the total number of ring atoms separating these two points of attachment, including the ring atoms at the points of attachment, is an odd whole number.

Another object of this invention is to provide improved enzymatically cleavable chemiluminescent 1,2-dioxetane compounds which, upon decomposition, emit light of greater intensity than the light emitted by isomers thereof and which also exhibit a shift in the wavelength of the light emitted as compared to the wavelengths of light emitted by the corresponding even pattern substituted compounds.

A still further object of this invention is the use of these improved enzymatically cleavable chemiluminescent 1,2-dioxetane compounds to generate light in aqueous and non-aqueous media.

Yet another object of this invention is the use of these improved enzymatically cleavable chemiluminescent 1,2-dioxetane compounds in art-recognized immunoassays, chemical assays and nucleic acid probe assays, including multi-channel assays, to detect the presence or determine the concentration of chemical or biological substances, and as direct chemical/physical probes for studying the molecular structures or microstructures of various macromolecules: synthetic polymers, proteins, nucleic acids and the like.

These and other objects, as well as the nature, scope and utilization of this invention, will become readily apparent to those skilled in the art from the following description, the drawings and the appended claims.

DETAILED DESCRIPTION OF THE INVENTION

The improved enzymatically cleavable chemiluminescent 1,2-dioxetanes of this invention can be represented by the general formula:

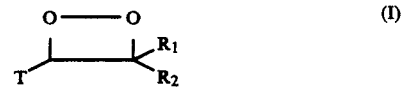

In this formula the symbol $R_1$ represents hydrogen, or a bond when $R_2$ represents a substituent bound to the dioxetane ring through a spiro linkage, or an organic substituent that does not interfere with the production of light and that satisfies the valence of the dioxetane ring carbon atom to which it is attached to result in a tetravalent dioxetane ring carbon atom, such as an alkyl, aryl, aralkyl, alkaryl, heteroalkyl, heteroaryl, cycloalkyl or cycloheteroalkyl group, e.g., a straight or branched chain alkyl group having from 1 to 7 carbon atoms, inclusive; a straight or branched chain hydroxyalkyl group having from 1 to 7 carbon atoms, inclusive, an —OR group in which R is a $C_1$–$C_{20}$ unbranched or branched, unsubstituted or substituted, saturated or unsaturated alkyl, cycloalkyl, cycloalkenyl, aryl, aralkyl or aralkenyl group, any of which may additionally be fused to $R_2$ such that the emitting fragment contains a lactone ring, fused ring cycloalkyl, cycloalkenyl, aryl, aralkyl or aralkenyl group, or an N, O or S heteroatom-containing group. Preferably, $R_1$ is a methoxy group.

The symbol $R_2$ represents a fused polycyclic ring-containing fluorophore moiety having an enzymatically cleavable labile ring substituent containing a bond which, when cleaved by an enzyme, renders the fused polycyclic moiety electron-rich to in turn render the dioxetane compound decomposable to emit light. This labile ring substituent's point of attachment to the fused polycyclic ring, in relation to this ring's point(s) of attachment to the dioxetane ring (single bond attachment or a spiro linkage), is such that the total number of ring atoms separating these points of attachment, including the ring atoms at the points of attachment, is an odd whole number.

Included among the fused polycyclic ring compounds whose residues can be used to form this fluorophore moiety are fused polycyclic aromatic hydrocarbon ring fluorophoric compounds containing from 9 to about 30 ring carbon atoms, inclusive, such as naphthalene:

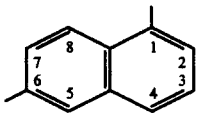

the substituent bonds indicating a 1,6-substitution pattern as in 3-(2'-spiroadamantane)-4-methoxy-4-(6''-disodiumphosphoryloxy)-naphth-1'-yl-1,2-dioxetane, pentalene, azulene, heptalene, asindacene, s-indacene, biphenylene, perylene, acenaphthylene, phenanthrene, anthracene, acephenanthrylene, aceanthrylene, triphenylene, pyrene, chrysene, naphthacene, and the like, as well as derivatives thereof substituted with one or more non-labile substituents such as a branched or straight chain alkyl group having 1 to 20 carbon atoms, inclusive, e.g., methyl, n-butyl or decyl, a branched or straight chain heteroalkyl group having 1 to 7 carbon atoms, inclusive, e.g., methoxy, hydroxyethyl or hydroxypropyl; an aryl group having 1 or 2 rings, e.g., phenyl; a heteroaryl group having 1 or 2 rings, e.g., pyrrolyl or pyrazolyl; a cycloalkyl group having 3 to 7 carbon atoms, inclusive, in the ring, e.g., cyclohexyl; a heterocycloalkyl group having 3 to 6 carbon atoms, inclusive, in the ring, e.g., dioxane; an aralkyl group having 1 or 2 rings, e.g., benzyl; an alkaryl group having 1 or 2 rings, e.g., tolyl; an electron-withdrawing group, such as a perfluoroalkyl group having between 1 and 7 carbon atoms, inclusive, e.g., trifluoromethyl; a halogen; $CO_2H$, $ZCO_2H$, $SO_3H$, $NO_2$, $ZNO_2$, $C\equiv N$, or $ZC\equiv N$, where Z is a branched or straight chain alkyl group having 1 to 7 carbon atoms, inclusive, e.g., methyl, or an aryl group having 1 or 2 rings, e.g., phenyl; an electron-donating group, e.g., a branched or straight chain $C_1$-$C_7$ alkoxy group, e.g., methoxy or ethoxy: an aralkoxy group having 1 or 2 rings, e.g., phenoxy; a branched or straight chain $C_1$-$C_7$ alkoxy group, e.g., methoxy or ethoxy; an aralkoxy group having 1 or 2 rings, e.g., phenoxy; a branched or straight chain $C_1$-$C_7$ hydroxyalkyl group, e.g., hydroxymethyl or hydroxyethyl; a hydroxyaryl group having 1 or 2 rings, e.g., hydroxyphenyl; a branched or straight chain $C_1$-$C_7$ alkyl ester group, e.g., acetate; an aryl ester group having 1 or 2 rings, e.g., benzoate; or a heteroaryl group having 1 or 2 rings, e.g., benzoxazole, benzthiazole, benzimidazole or benztriazole.

The fused polycyclic ring portion of the fluorophore moiety represented by $R_2$ can also be the residue of a nonaromatic, i.e., less than fully aromatic, fused polycyclic hydrocarbon ring fluorophoric compound, having an enzymatically cleavable labile ring substituent containing a bond which, when cleaved by an enzyme, renders the fused, less than fully aromatic polycyclic moiety electron-rich to in turn render the dioxetane compound decomposable to emit light, unsubstituted or substituted with one or more of the aforementioned non-labile substituents, and containing from 10 to about 30 ring carbon atoms, inclusive, such as fluorene, dibenzosuberene, 9,10-dihydrophenanthrene, indene, indeno [1,2-a]indene, phenalene, fluoroanthrene, and the like.

Further, the fused polycyclic ring portion of the fluorophore moiety represented by $R_2$ can also be the residue of a fused polycyclic aromatic or nonaromatic heterocyclic ring fluorophoric compound, e.g., benzo[b]thiophene, naphtho[2,3-b]thiophene, thianthrene, benzofuran, isobenzofuran, chromene, xanthene, phenoxathiin, quinoline, isoquinoline, phenanthridine, phenazine, phenoxazine, phenothiazine, phenanthroline, purine, 4H-quinolizine, phthalazine, naphthyridine, indole, indolizine, chroman, isochroman, indoline, isoindoline, and the like, unsubstituted or substituted with one or more of the aforementioned non-labile substituents, and containing from 9 to about 30 ring atoms, inclusive, the bulk of which are carbon atoms.

Included among the enzymatically cleavable labile ring substituents which can be positioned on a fused polycyclic ring to make up the fluorophore moieties of this invention are substituents which, when cleaved, yield an oxygen anion, a sulfur anion, or a nitrogen anion such as a sulfonamido anion. Such enzymatically cleavable substituents include phosphate ester groups represented by the general formula:

 (II)

wherein M+ represents a cation such as alkali metal, e.g., sodium or potassium, ammonium, or a $C_{1-7}$ alkyl, aralkyl or aromatic quaternary ammonium cation, $N(R_3)_4+$ in which each $R_3$ can be alkyl, e.g., methyl or ethyl, aralkyl, e.g., benzyl, or form part of a heterocyclic ring system, e.g., pyridinium, and particularly the disodium salt. Such quaternary ammonium cations can also be connected through one of their quaternizing groups to a polymeric backbone, viz.

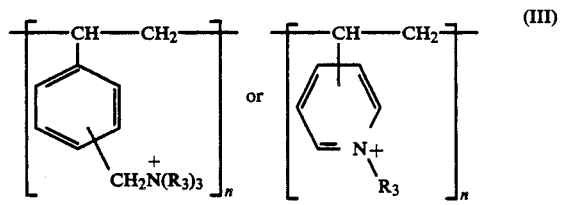 (III)

where n is greater than 1, or can be part of a polyquaternary ammonium salt, i.e., an ionene polymer.

Enzymatically cleavable substituents also include enzyme-cleavable alkanoyloxy groups, e.g., an acetate ester group, or an enzyme-cleavable oxacarboxylate group, 1-phospho-2,3-diacylglyceride group, 1-thio-D-glucoside group, adenosine triphosphate analog group, adenosine diphosphate analog group, adenosine monophosphate analog group, adenosine analog group, α-D-galactoside group, β-D-galactoside group, α-D-glucoside group, β-D-glucoside group, α-D-mannoside group, β-d-mannoside group, β-D-fructofuranoside group, β-D-glucosiduronate group, p-toluenesulfonyl-L-arginine ester group or p-toluenesulfonyl-L-arginine amide group.

$R_1$ and $R_2$ together can represent a labile group-substituted fused polycyclic ring-containing fluorophore moiety bonded to the 4-carbon atom of the dioxetane ring through a spiro linkage, e.g., a 6-disodiumphosphoryloxy-2-oxa-1,2,3,4-tetrahydrophenanthr-1-ylidene group.

The symbol T represents a stabilizing group that prevents the dioxetane compound from decomposing before the bond in the enzymatically cleavable labile ring substituent on the fused polycyclic ring-containing fluorophore moiety is intentionally cleaved, such as an unsubstituted or substituted cycloalkyl, aryl, including fused aryl, or heteroaryl group, e.g., an unsubstituted cycloalkyl group having from 6 to 12 ring carbon atoms, inclusive; a substituted cycloalkyl group having from 6 to 12 ring carbon atoms, inclusive, and having one or more substituents which can be an alkyl group having from 1 to 7 carbon atoms, inclusive, or a heteroatom group which can be an alkoxy group having from 1 to 12 carbon atoms, inclusive, such as methoxy or ethoxy, a substituted or unsubstituted aryloxy group, such as phenoxy or carboxyphenoxy, or an alkoxyalkyloxy group, such as methoxyethoxy or polyethyleneoxy, or a cycloalkylidene group bonded to the 3-carbon atom of the dioxetane ring through a spiro linkage and having from 6 to 12 carbon atoms, inclusive, or a fused polycycloalkylidene group bonded to the 3-carbon atom of the dioxetane ring through a spiro linkage and having two or more fused rings, each having from 5 to 12 carbon atoms, inclusive, e.g., an adamant-2-ylidene group.

One or more of the substituents $R_1$, $R_2$ and T can also include a substituent which enhances the water solubility of the 1,2-dioxetane, such as a carboxylic acid, e.g., acetic acid, sulfonic acid, e.g., methanesulfonic acid or ethanesulfonic acid, or quaternary amino salt group, e.g., ammonium bromide.

A preferred class of odd pattern substituted fused polycyclic ring-containing 1,2-dioxetanes coming within the scope of this invention are 3-(2'spiroadamantane)-4-methoxy-4-(phosphoryloxy)naphth-2'-yl-1,2-dioxetane salts such as those represented by the formulas:

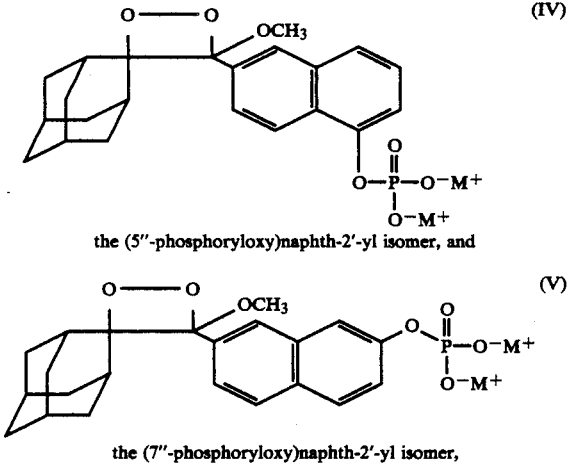

the (5''-phosphoryloxy)naphth-2'-yl isomer, and the (7''-phosphoryloxy)naphth-2'-yl isomer, wherein M+ is as described for formula II above.

The improved enzymatically cleavable chemiluminescent 1,2-dioxetanes of this invention can be synthesized in known manner, e.g., by a reaction scheme involving first the synthesis of an olefin represented by the general formula:

e.g., an enol ether such as:

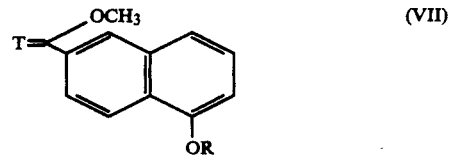

wherein T and R are as described for formula I above, using a Wittig reaction or the methods described in the aforementioned copending Edwards application. Incorporation of an enzymatically cleavable labile ring substituent on the fused polycyclic ring and photochemical or chemical conversion to the corresponding 1,2-dioxetane can then be accomplished as described in the aforementioned copending Bronstein and Edwards applications.

Key intermediates in the synthesis of the improved fused polycyclic aromatic hydrocarbon ring-containing chemiluminescent 1,2-dioxetanes of this invention by methods such as those described in the aforementioned copending Edwards application are, first of all, fused polycyclic aromatic hydrocarbon ring-containing fluorophoric compounds having from 9 to about 30 carbon atoms, inclusive, and having at least an ether substituent, which can be an —OR group as defined above, e.g., an alkoxy or silyloxy group such as a methoxy or t-butyldimethylsilyloxy group, and a halo substituent, i.e., a chlorine, bromine or iodine atom, with the total number of ring carbon atoms separating these two substituents, including the carbon atoms to which they are attached, being an odd whole number. Such intermediates include, for example, fused polycyclic aromatic hydrocarbon ring-containing fluorophoric compounds such as:
2-chloro-7-methoxynaphthalene,
2-bromo-7-methoxynaphthalene,
2-iodo-7-methoxynaphthalene,
1-chloro-8-methoxynaphthalene,
1-bromo-8-methoxynaphthalene,
1-iodo-8-methoxynaphthalene,
2-chloro-5-methoxynaphthalene,
2-bromo-5-methoxynaphthalene,
2-iodo-5-methoxynaphthalene,
1-chloro-6-methoxynaphthalene,
1-bromo-6-methoxynaphthalene,
1-iodo-6-methoxynaphthalene,
2-chloro-10-methoxyanthracene,
2-bromo-10-methoxyanthracene,
2-iodo-10-methoxyanthracene,
and the like.

These iodo-substituted ethers can be prepared from the corresponding ether triazenes in the manner described in Example I, infra, using an alkali metal halide such as potassium iodide and an acidic resin. The other halo-substituted ethers can be prepared from the corresponding diazonium salts using $Ca_2Cl_2/HCl$ or $CuBr/HBr$, or by chlorination or bromination and subsequent oxidation of various methoxy 1-or 2-tetralones, as described in Example VIII, infra.

Also key to such synthetic methods are the next two intermediates in the sequence given, inter alia, in Example I, infra, i.e., the alcohols and ketones having the general formulas:

(VIII)

(IX)

wherein T is as described for formula I above and $R_4$ is the ether substituted residue of the ether and halogen substituted fluorophoric fused polycyclic aromatic hydrocarbon ring-containing compound, in which residue the total number of carbon atoms separating the ring carbon atom to which the ether substituent is attached and the ring carbon atom through which this residue, $R_4$, is attached to the remainder of the alcohol or ketone molecule (the ring carbon atom to which the precursor intermediate's halogen substituent was attached), including the carbon atoms at the points of attachment, is, once again, an odd whole number. Such alcohol and ketone intermediates include, for example:
7-methoxynaphth-2-yladamant-2'-yl alcohol,
8-methoxynaphth-2-yladamant-1'-yl alcohol,
5-methoxynaphth-2-yladamant-2'-yl alcohol,
6-methoxynaphth-2-yladamant-1'-yl alcohol,
7-methoxynaphth-2-yladamant-2'-yl ketone,
8-methoxynaphth-2-yladamant-1'-yl ketone,
5-methoxynaphth-2-yl-adamant-2'-yl ketone,
6-methoxynaphth-2-yl-adamant-1'-yl ketone,
and the like.

As will be apparent to those skilled in the art, the odd patterned halo, hydroxy fused polyoyclic aromatic hydrocarbons, analogous to the above-listed haloethers and obtainable from these haloethers by cleavage with HBr in acetic acid or by other known methods, are also useful precursors of the improved enzymatically cleavable chemiluminescent 1,2-dioxetanes of this invention. For example, the synthetic method given, inter alia, in Example IX infra can be modified by reacting a 6-halo-1-naphthol, e.g., 6-bromo-1-naphthol, directly with two equivalents of n-butyllithium to generate a dianion which can subsequently be reacted with one equivalent of adamantane-2-carboxaldehyde to generate an alcohol of general formula VIII above, where $R_4$ is a hydroxy rather than an ether substituted residue. Such hydroxy- and halo-substituted intermediates include, for example:
2 chloro-7-hydroxynaphthalene,
2-bromo-7-hydroxynaphthalene,
2-iodo-7-hydroxynaphthalene,
1-chloro-8-hydroxynaphthalene,
1-bromo-8-hydroxynaphthalene,
1-iodo-8-hydroxynaphthalene,
2-chloro-5-hydroxynaphthalene,
2-bromo-5-hydroxynaphthalene,
2-iodo-5-hydroxynaphthalene,
1-chloro-6-hydroxynaphthalene,
1-bromo-6-hydroxynaphthalene,
1-iodo-6-hydroxynaphthalene,
2-chloro-0-hydroxyanthracene,
2-bromo-10-hydroxyanthracene,
2-iodo-10-hydroxyanthracene, and the like.

The improved enzymatically cleavable chemiluminescent 1,2-dioxetanes of this invention are particularly useful as the means of identifying or quantifying an analyte or several analytes using otherwise art-recognized immunoassays, such as those employed to detect an enzyme or a member of a specific binding pair, e.g., an antigen-antibody pair or a nucleic acid paired with a probe capable of binding to all or a portion of the nucleic acid. Such assays include immunoassays used to detect a hormone such as β-HCG, thyroid stimulating hormone (TSH), follicle stimulating hormone (FSH), HLH or the like, cell surface receptor assays, and nucleic acid probe assays used to detect viruses, e.g., HIV or HTLV III, herpes simplex virus (HSV), human papiloma virus (HPV), and cytomegalovirus (CMV), or bacteria, e.g., *E. Coli.*, and histocompatibility assays; for typical assay protocols see working examples X and XI, infra as well as the aforementioned copending Bronstein and Bronstein et al applications.

As noted above, by using two or more of the improved enzymatically cleavable chemiluminescent 1,2-dioxetanes of this invention that each emit light of a different wavelength from the others, or by using one or more of these different colored light-emitting improved enzymatically cleavable chemiluminescent 1,2-dioxetanes with one or more other chemiluminescent compounds which emit light of yet other wavelengths, each of such compounds being structured so as to be decomposable by a different means, a multi-channel assay can be designed in which different cleaving means, and especially two or more different enzymes, attached to or associated with two or more different analytes will, by cleaving different cleavable dioxetane substituents, induce the emission of light of a different wavelength for each analyte being assayed.

3-(2'-Spiroadamantane)-4-methoxy-4-(3'-disodiumphosphoryl- oxy)phenyl-1,2-dioxetane, for example, when cleaved with an alkaline phosphatase, will emit blue light, 3-(2'-spiroadamantane)-4-methoxy-4-(7''-acetoxy)naphth-2'-yl-1,2-dioxetane, when cleaved with base or a carboxylesterase, will emit green light, and 3-(2'-spiroadamantane)-4-methoxy-4-(5''-β-galactosyloxy)naphth-2'-yl-1,2-dioxetane, when cleaved with a β-galactosidase, will emit orange light. A simultaneous assay for HSV, CMV and HPV can hence be designed using these three chemiluminescent substances to produce light emissions of a different color for each of these three analytes; see Example XI, infra.

Light of various colors emitted when using chemiluminescent 1,2-dioxetanes singly or in combinations as discussed above to identify or quantify various analytes can also be used to make a permanent record of such emissions on color photographic emulsions or specially sensitized black and white high speed films. Also, these chemiluminescent 1,2-dioxetanes can be used to achieve a matched response by detectors: charged coupled devices (CCD's) or silicon photodiodes, for example, having maximum sensitivity for a color other than blue, e.g., green or red. Thus for example, the blue light emitted when 3-(2'-spiroadamantane)-4-methoxy-4-(6''-disodiumphosphoryloxy)naphth-2'-yl-1,2-dioxetane is cleaved by an alkaline phosphatase to detect β-HCG can be changed to green light simply by replacing this phosphoryloxy naphthyl dioxetane with its odd pattern substituted isomer, 3-(2'-spiroadamantane)-4-methoxy-4-(7''-disodiumphosphoryloxy)naphth-2'-yl-1,2-dioxetane. And by using the enhanced intensity enzymatically-cleavable chemiluminescent 1,2-dioxetanes of this invention together with a light absorbing/light shifting auxiliary fluorophore/light enhancer substance which absorbs light of one wavelength and in turn emits light of a different wavelength, e.g., a phycobiliprotein (phycobiliproteins are naturally-occurring substances in which a fluorophore is bonded to a protein), such as phycocyanine or phycoallocyanine, that will absorb the green light emitted by 3-(2'-spiroadamantane)-4-methoxy-4-(7"'-disodiumphosphoryloxy)naphth-2'-yl-1,2-dioxetane and reemit this light as red light, matched responses by color photographic emulsions that exhibit a poor response to blue light, a better response to green light but the best response to red light can also be achieved.

Besides the phycobiliproteins, other auxiliary fluorophores extraneous to the light-emitting fluorophores produced by the decomposition of the improved enzymatically cleavable chemiluminescent 1,2-dioxetane compounds of this invention that will accept energy, especially light, from these light-emitting fluorophores and in turn emit detectable energy, again preferably light, can be used when practicing this invention. Among such auxiliary fluorophores that can be used, alone or in combination, are the following substances whose residues can be present in known 1,2-dioxetanes and, in certain cases, if substituted with an enzymatically cleavable labile ring substituent in the appropriate odd numbered pattern, in the improved chemiluminescent 1,2-dioxetanes of this invention as well, as fluorescent chromophore groups:

anthracene and anthracene derivatives, e.g., 9,10-diphenylanthracene, 9-methylanthracene, 9-anthracene carboxaldehyde, anthryl alcohols and 9-phenylanthracene;

rhodamine and rhodamine derivatives, e.g., rhodols, tetramethyl rhodamine, tetraethyl rhodamine, diphenyldimethyl rhodamine, diphenyldiethyl rhodamine and dinaphthyl rhodamine;

fluorescein and fluorescein derivatives, e.g., 5-iodoacetamido fluorescein, 6-iodoacetamido fluorescein and fluorescein-5-maleimide;

coumarin and coumarin derivatives, e.g., 7-dialkylamino-4-methylcoumarin, 4-bromomethyl-7-methoxycoumarin and 4-bromomethyl-7-hydroxy coumarin;

erythrosin and erythrosin derivatives, e.g., hydroxy erythrosins, erythrosin-5-iodoacetamide and erythrosin-5-maleimide;

aciridine and aciridine derivatives, e.g., hydroxy aciridines and 9-methyl aciridine;

pyrene and pyrene derivatives, e.g., N-(1-pyrene) iodoacetamide, hydroxy pyrenes and 1-pyrenemethyl iodoacetate;

stilbene and stilbene derivatives, e.g., 6,6'-dibromostilbene and hydroxy stilbenes;

naphthalene and naphthalene derivatives, e.g., 5-dimethylamino naphthalene-1-sulfonic acid and hydroxy naphthalenes;

nitrobenzoxadiazoles and nitrobenzoxadiazole derivatives, e.g., hydroxy nitrobenzoxadiazoles, 4-chloro-7-nitrobenz-2-oxa-1,3-diazole, 2-(7-nitrobenz-2-oxa-1,3-diazol-4-yl) methylaminoacetaldehyde and 6-(7-nitrobenz-2-oxa-1,3-diazol-4-yl-aminohexanoic acid;

quinoline and quinoline derivatives, e.g., 6-hydroxyquinoline and 6-aminoquinoline;

acridine and acridine derivatives, e.g., N-methylacridine and N-phenylacridine;

acidoacridine and acidoacridine derivatives, e.g., 9-methylacidoacridine and hydroxy-9-methylacidoacridine;

carbazole and carbazole derivatives, e.g., N-methylcarbazole and hydroxy-N-methylcarbazole;

fluorescent cyanines, e.g., DCM (a laser dye), hydroxy cyanines, 1,6-diphenyl-1,3,5-hexatriene, 1-(4-dimethyl aminophenyl)-6-phenylhexatriene and the corresponding 1,3-butadienes;

carbocyanines and carbocyanine derivatives, e.g., phenylcarbocyanine and hydroxy carbocyanines;

pyridinium salts, e.g., 4-(4-dialkyldiaminostyryl)N-methyl pyridinium iodate and hydroxy-substituted pyridinium salts;

oxonols; and resorofins and hydroxy resorofins.

When such auxiliary fluorophores are bonded to a chemiluminescent compound, they are preferably bonded to the portion of the chemiluminescent compound that, upon decomposition, forms a fragment containing the fluorophore portion of the chemiluminescent compound's molecule. In this way energy transfer is enhanced due to the two fluorophores being in close proximity to one another and by beneficial spatial arrangements provided by the rigidity of the microenvironment. Auxiliary fluorophores that are insoluble or partially insoluble in aqueous medium can be solubilized by first grafting them onto solubilizing molecules, e.g., water soluble oligomer or polymer molecules.

And, in all cases, enhancement of the intensity of the light emitted by decomposition of the improved enzymatically cleavable chemiluminescent 1,2-dioxetane compounds of this invention in aqueous media can be achieved by the methods disclosed in the aforementioned Voyta et al application.

In order that those skilled in the art can more fully understand this invention, the following examples are set forth. These examples are given solely for purposes of illustration, and should not be considered as expressing limitations unless so set forth in the appended claims. All parts and percentages are by weight, unless otherwise stated.

EXAMPLE I

[Synthesis of 3-(2'-spiroadamantane)-4-methoxy-4-(7"'-acetoxy)-naphth-2'-yl-1,2-dioxetane]; an enzymatically and chemically chemiluminescent 1,2-dioxetane 2-Amino-7-hydroxynaphthalene. To a solution of 2,7-dihydroxynaphthalene (27.56 g, 0.172 mol) in 30% $NH_4OH$ (200 ml) was added $NaHSO_3$ (19.03 g, 0.183 mol) at 0° C. with stirring. The Bucherer reaction was then carried out by heating the solution in a steel bomb at 150° C. for 4.5 hours, giving both mono- and diaminonaphthalenes in a 1:1 ratio. Subsequently, the cooled product mixture was dissolved in $EtOAc/CH_3CN$ (ethyl acetate/methyl cyanide), partitioned with 1M NaOH, followed by washing the organic layer with NaOH until the washes were clear. The combined NaOH layers were acidified to pH 1, partitioned with minimal EtOAc to remove traces of starting material and then carefully neutralized to pH 7 with NaOH pellets. Upon partitioning the aqueous layer with EtOAc, the organic layer was dried over $Na_2SO_4$ and evaporated to yield 12.49 g (45.7%) of 2-amino-7-hydroxynaphthalene as light tan crystals, m.p. 186°–188° C.

IR (Nujol, $cm^{-1}$): 3401, 3323, 3313, 1629, 1512, 1301, 1216, 883, 831

2-Amino-7-methoxynaphthalene. 2-Amino-7-hydroxynaphthalene (18.6 g, 0.117 mol) was added in portions to hexane-rinsed NaH (60%, 5.1 g, 0.127 mol) in dry DMF (dimethylformamide; 100 ml) at 0° C. The solution was stirred under argon for 10 minutes until hydrogen evolution had ceased, whereupon dimethyl sulfate (11 ml, 0.116 mol) was added dropwise via syringe at 0° C. until O-methylation was complete by TLC monitoring. The reaction was carefully quenched with 6N HCl to pH 1, and partitioned between ether and water, thus separating the naphthylamine hydrochloride from organic impurities. After washing the ether layer with 6N HCl, the aqueous layers were combined, neutralized with NaOH pellets to pH 8 and partitioned with EtOAc to recover the free amine in the organic layer. The basic aqueous layer was washed twice with EtOAc, and the combined EtOAc layers were dried over $Na_2SO_4$ and evaporated. Upon removal of DMF under high vacuum, the product mixture crystallized. Crystals of 2-amino-7-methoxynaphthalene (19.4 g, 96.5%) were collected from MeOH, m.p. 157° C.

IR (Nujol, $cm^{-1}$): 3403, 3318, 1628, 1511, 1213, 1028, 871, 826

NMR ($CDCl_3$, ppm): 3.84 (2H, br s); 3.90 (3H, s); 6.73–7.00 (4H, m); 7.54–7.60 (2H)

2-Iodo-7-methoxynaphthalene. Diazotization of 2-amino-7-methoxynaphthalene (17.02 g, 0.098 mol) in 20% aqueous HCl (81.4 ml, 0.197 mol HCl), proceeded smoothly by adding $NaNO_2$ (7.11 g, 0.103 mol) in 65 ml $H_2O$ dropwise at 0° C. The reaction was stirred for 1 hour, adding a small amount of EtOAc to reduce foaming as needed. To form the triazene, a solution of $K_2CO_3$ (20.41 g, 0.148 mol), diethylamine (15.3 ml, 0.148 mol) and $H_2O$ (60 ml) was added dropwise to the cooled diazonium salt. After adding ethyl ether (30 ml) to dissolve the newly formed naphthalene triazene, followed by stirring for 35 minutes at low temperature, the reaction solution was poured into a separatory funnel and the aqueous layer was drawn off. The ether layer was washed with $H_2O$, dried over $Na_2SO_4$ and evaporated under reduced pressure with low heat, giving an orange oil. The crude diethyltriazene was used immediately without purification.

2-(3',3'-Diethyl)triazo-7-methoxynaphthalene, dissolved in 120 ml dry $CH_3CN$, was added dropwise (1 drop/4 seconds) to a slurry of ground KI (49.12 g, 0.296 mol), Amberlyst XN-1010 acidic resin (Aldrich Chemical Co.; 37.3 g), and ground molecular sieves in dry $DMF/CH_3CN$ (50 ml/150 ml) at 70° C. overnight. Upon complete conversion of the triazene to the iodide, the cooled solution was carefully decanted into a separatory funnel, rinsing the resin with two EtOAc washes. The organic material was partitioned between EtOAc and $H_2O$, collecting the EtOAc layer, which was dried over $Na_2SO_4$ and evaporated.

To purify the iodonaphthalene, the crude reaction mixture was dissolved in $CH_3CN$ and partitioned with hexanes until all desired iodide had been removed from the $CH_3CN$ layer. The hexanes solution was evaporated to yield, upon addition of petroleum ether, acrid orange crystals of 2-iodo-7-methoxynaphthalene (10.36 g, 33.1% m.p. 116° C.). [Literature reference: *J.Org.-Chem.*, (1983) 48, 4396.]

IR ($CHCl_3$, $cm^{-1}$): 3005, 1625, 1504, 1458, 1394, 1359, 1250, 1176, 1126, 1031, 958, 916, 886, 841, 631

NMR ($CDCl_3$, ppm): 3.82 (3H, s); 6.91 (1H, d, J=2.44 Hz); 7.05 (1H, dd, J=8.9, 2.5 Hz); 7.39 (1H, d, J=8.47 Hz); 7.05 (1H, dd, J=8.9, 2.5 Hz); 7.39 (1H, d, J=8.47 Hz); 7.47 (1H, d, J=8.46 Hz); 7.59 (1H, d, J=9.0 Hz); 8.04 (1H, s)

By using halogenating agents such as $Cu_2Cl_2$/HCl and CuBr/HBr in combination with the diazonium salt intermediate instead of the triazene, 2-chloro-7-methoxynaphthalene and 2-bromo-7-methoxynaphthalene are obtained.

7-Methoxynaphth-2-yladamant-2'-yl alcohol. Lithiation of 2-iodo-7-methoxynaphthalene (508.1 mg, 1.79 mmol) in 5 ml anhydrous ether proceeded cleanly upon addition of n-BuLi (n-butyllithium; 1.6M, 1.2 ml) at 0° C. under argon. Dropwise addition of adamantane-2-carboxaldehyde, dissolved in anhydrous ether (2 ml), to the naphthyllithium solution immediately yielded the coupled lithium alkoxide. The reaction was quenched by partitioning between $EtOAc/H_2O$, washing the aqueous layer twice with EtOAC to completely recover the polar alcohols. The combined organic layers were dried over $Na_2SO_4$, evaporated and the residual oil was chromatographed on silica gel, eluting with 20% EtOAc/hexanes, to give an off-white crystalline alcohol mixture (437.9 mg, 76%)

IR, less polar alcohol ($CHCl_3$, $cm^{-1}$): 3601, 3005, 2905, 2846, 1632, 1607, 1515, 1465, 1391, 1265, 1175, 1125, 1034, 895, 845, 705

IR, polar alcohol ($CHCl_3$, $cm^{-1}$): 3589, 3005, 2905, 2849, 1631, 1609, 1515, 1465, 1393, 1259, 1137, 1129, 1035, 845, 805, 680

7-Methoxynaphth-2-yladamant-2'-yl ketone. The 7-methoxynaphth-2-yladamant-2'-yl epimeric alcohols (238 mg, 0.739 mmol) in 6 ml acetone were oxidized by dropwise addition of Jones reagent at 0° C. until analytical TLC indicated complete conversion to the ketone. The reaction mixture was partitioned between EtOAc and $H_2O$ and the aqueous layer was washed three times with EtOAc. The combined EtOAc layers were washed with minimal saturated $NaHCO_3$ solution, dried through a $Na_2SO_4$ column, and evaporated to a light yellow oil. The crude ketone was used without purification. A small amount was chromatographed (5% EtOAc/hexanes) and crystallized from acetone as a fine white powder, m.p. 116° C.

IR ($CHCl_3$, $cm^{-1}$): 2908, 2846, 1674 (C=O), 1629, 1605, 1466, 1272, 1257, 1179, 1132, 1126, 1105, 1035, 844

NMR ($CDCl_3$, ppm): 1.59–2.13 (12H); 2.39 (2H, s); 3.59 (1H, s); 3.94 (3H, s); 7.23 (1H, s); 7.245 (1H, d, J=3.61 Hz); 7.74 (1H, d, J=3.17 Hz); 7.76 (1H, d, J=8.30 Hz); 7.80 (1H, d, J=8.36 Hz); 8.24 (1H, s)

Methoxy(7-methoxynaphth-2-yl)methylene adamantane. Anion formation of 7-methoxynaphth-2-yladamant-2'-yl ketone (236 mg, 0.739 mmol) occurred at 50° C. in the presence of potassium t-butoxide (150.6 mg, 1.34 mmol) in 3.5 ml of DMSO under argon. After stirring for 5 minutes, addition of dimethyl sulfate (120 μl, 1.27 mmol) gave O-methylation, with a trace of ketone remaining. The cooled solution was partitioned with $EtOAc/H_2O$ and the EtOAc layer was dried through a $Na_2SO_4$ column and evaporated. A small amount of the residual oil was separated on an analytical TLC plate (silica gel) for spectroscopic characterization. The crude enol ether was used in the next step without purification.

IR ($CHCl_3$, $cm^{-1}$): 2905, 2843, 1627, 1604, 1510, 1463, 1214, 1124, 1091, 1033, 848

Methoxy(7-acetoxynaphth-2-yl)methylene adamantane. Crude methoxy(7-methoxynaphth-2-yl)methylene adamantane (247 mg, 0.739 mmol) was added to sodium ethylthiolate (62 mg, 0.743 mmol) in dry DMF (4 ml)

and the solution was refluxed under argon for 4 hours deprotecting the aromatic methoxy moiety to the naphthol. Excess sodium ethanethiolate (122 mg, 1.45 mmol) was added in two portions during the reflux to push the demethylation to completion. The naphthol was worked up by partitioning the cooled solution between EtOAc and minimal H$_2$O. Traces of naphthol in the aqueous layer were recovered with two EtOAc washes. The EtOAc layers were dried and evaporated. The crude naphthol was immediately acylated upon dissolution in acetic anhydride (1 ml) and pyridine (2 ml) with gentle warming to 50° C. After evaporation, the reaction mixture was chromatographed on a silica gel column prewashed with 10% EtOAc/hexanes containing 1% triethylamine, eluting with the same EtOAc/hexanes/TEA solvent mixture. The four-step reaction sequence—oxidation, enol ether formation, aromatic demethylation and acylation—gave 69.3 mg (25.8%) of methoxy(7-acetoxynaphth-2-yl)methylene adamantane, m.p. 125° C.

IR (CH$_2$Cl$_2$, cm$^{-1}$): 2897, 2847, 1757, 1629, 1606, 1508, 1448, 1372, 1212, 1198, 1157, 1104, 1092, 1083, 1017, 968, 919, 849

NMR (CDCl$_3$, ppm): 1.8–2.0 (13H); 2.38 (3H, s); 2.69 (1H, br s); 3.3 (3H, s); 7.21 (1H, dd, J=9.0, 2.5 Hz); 7.44 (1H, dd, J=8.5, 1.5 Hz); 7.54 (1H, d, J=1.6 Hz); 7.71 (1H,s); 7.82 (1H, d, J=8.0 Hz); 7.84 (1H, d, J=8.9 Hz)

3-(2'-spiroadamantane)-4-methoxy-4-(7"-acetoxy)-naphth-2'-yl-1,2-dioxetane. A solution of methoxy(7-acetoxynaphth-2-yl)-methylene admanantane (29.0 mg, 0.080 mmol) and methylene blue adsorbed on silica gel (97.9 mg, 2.6 mg dye/g SiO$_2$) in methylene chloride (12 ml) was irradiated with a 250 Watt high pressure sodium lamp at 10° C. while passing a stream of oxygen through the solution. A 5 mil thick piece of Kapton polyimide film (DuPont) placed between the lamp and the reaction mixture filtered unwanted UV radiation. TLC and UV monitoring showed complete dioxetane formation after irradiating for 25 minutes. The sensitizer was removed by filtration, the solvent was evaporated and the resulting crude oil was chromatographed on silica gel, eluting with 10% THF (tetrahydrofuran)/hexanes to give 26.0 mg (82%) of the 7"-acetoxynaphth-2'-yl dioxetane.

Starting with 1,8-dihydroxynaphthalene and proceeding through the same synthesis as in Example I gives:
1-amino-8-hydroxynaphthalene,
1-amino-8-methoxynaphthalene,
1-iodo-8-methoxynaphthalene,
8-methoxynaphth-2-yladamant-1'-yl alcohols,
8-methoxynaphth-2-yladamant-1'-yl ketone,
methoxy(8-methoxynaphth-1-yl)methylene adamantane,
methoxy(8-acetoxynaphth-1-yl)methylene adamantane, and
3-(2'-spiroadamantane)-4-methoxy-4-(8"-acetoxy)-naphth-1'-yl-1,2-dioxetane.
And by synthesizing:
methoxy(7-disodiumphosphoryloxynaphth-2-yl)-methylene adamantane, and
methoxy(8-disodiumphosphoryloxynaphth-1-yl)-methylene adamantane,
by phosphorylating the corresponding methoxynaphthyl compounds in the manner disclosed in the aforementioned copending Edwards application and then photooxygenating these phosphate esters as described in Example I above, the corresponding 1,2-dioxetanes:
3-(2'-spiroadamantane)-4-methoxy-4-(7"-disodiumphosphoryloxy)naphth-2'-yl-1,2-dioxetane, and
3-(2'-spiroadamantane)-4-methoxy-4-(8"-disodiumphosphoryloxy)naphth-1'-yl-1,2-dioxetane,
are obtained.

EXAMPLE II

[Synthesis of
3-(2'-spiroadamantane)-4-methoxy-4-(5"-acetoxy)-naphth-2'-yl-1,2-dioxetane and
3-(2'-spiroadamantane)-4-methoxy-4-(5"-phosphoryloxy)naphth-2'-yl-1,2-dioxetane].

2-Bromo-5-methoxynaphthalene. Under an argon atmosphere, 60% sodium hydride (1.4 g, 0.035 mol) is washed 3 times with hexanes. Sieve dried (3A) DMF (40 ml) is added and the suspension is cooled to 0° C. while 6-bromo-1-naphthol (5 g., 0.032 mol; Hodgson et al, *J.Chem.Soc.*, 8, 1944) is added with stirring. After hydrogen evolution ceases, dimethyl sulfate (3.4 ml, 0.036 mol) is added dropwise. Stirring is continued in the cold for 8 hours. The reaction mixture is diluted with 250 ml ice cold 0.05N NaOH to yield a gummy precipitate. The aqueous layer is decanted and the residue is triturated several times with dilute NaOH. Plug chromatography on silica gel (15% ethyl acetatehexanes) affords a good yield of the bromo ether.

R and S 5-methoxynaphth-2-yl-adamanat-2'-yl alcohol. 2-Bromo-5-methoxynaphthalene (500 mg., 2.1 mmol) is dissolved in 25 ml anhydrous ether under argon. The solution is cooled to 0° C. and treated with a solution of n-BuLi (1.6M in hexanes, 2 ml) via syringe. The resulting solution is stirred in the cold for 15 minutes prior to the addition of a solution of adamantane-2-carboxaldehyde (416 mg., 2.5 mmol) in 20 ml anhydrous ether. The mixture is slowly warmed to room temperature and quenched with 50 ml 1% NH$_4$Cl solution. The ether layer is removed, extracted again with water, and dried over Na$_2$SO$_4$. The solvent is stripped to afford an oil which is flash chromatographed on silica gel with 10% ethyl acetate-hexanes as eluant. The fractions containing the lower Rf isomeric alcohols are combined and concentrated to yield product in moderate yield.

5-Methoxynaphth-2-yladamant-2'-yl ketone. A solution of the 5-methoxynaphth-2-yl-adamant-2'-yl alcohols (700 mg., 2.17 mmol) in 20 ml acetone is cooled to 0° C. and treated dropwise with Jones reagent (23 ml conc. H$_5$O$_4$ and 26.9 g. CrO$_3$ and water to 100 ml) while stirring vigorously. The rapid reaction is monitored by TLC until the lower Rf starting material is replaced by the less polar ketonic product. The greenish yellow mixture is partitioned between 60 ml ethyl acetate and water. The aqueous layer, which contains some solid, is extracted three times with ethyl acetate (20 ml). The combined organic fractions are washed with saturated NaHCO$_3$ solution, dried over Na$_2$SO$_4$, and stripped to a light yellow oil which exhibits the characteristic carbonyl stretch in the infrared spectrum. The crude product is used directly for conversion to the enol ether.

Methoxy (5-methoxynaphth-2-yl) methylene adamantane. A solution of the crude 5-methoxynaphth-2-yladamant-2'-yl ketone (1 g., 3.1 mmol) in 35 ml sieve dried (3A) DMSO at 50° C., is treated with potassium tert-butoxide (0.7 g., 6.3 mmol) under a leisurely flow of argon. The colored solution of the enolate anion is stirred for 10 minutes. The solution becomes decolorized during a 15 minute dropwise addition of dimethyl sulfate (595 μl, 6.3 mmol). After cooling to room temperature the solution is stirred overnight and partitioned between ethyl acetate and water. The organic layer is washed three times with water and dried over anhydrous $K_2CO_3$. Concentration in vacuum yields an oil which is immediately plug chromatographed on silica gel with 5% ethyl acetate hexanes to yield the enol ether in good yield. TLC analysis in the same solvent system shows that a trace of the more polar ketonic starting material is present as a contaminant.

Methoxy-5(5-hydroxynaphth-2-yl)methylene adamantane. Under an argon atmosphere, 60% sodium hydride (200 mg, 5 mmol) is washed twice with hexanes. Excess solvent is blown off and sieve-dried DMF (15 ml) is added. The resulting slurry is cooled to 0° C. with stirring. Ethanethiol (370 µl, 5 mmol) is added dropwise via syringe. After 10 minutes the mixture is warmed to room temperature and stirred until hydrogen evolution abates. Methoxy-(5-methoxynaphth-2-yl)methylene adamantane (750 mg., 2.24 mmol) in 10 ml DMF is added all at once and the resulting solution is refluxed for 3.5 hours. DMF is removed in vacuuo and the residue is partitioned between 5% $NH_4Cl$ and 25 ml ethyl acetate. The aqueous layer is extracted again with another equivalent volume of ethyl acetate. The combined organic layers are washed with $2 \times 30$ ml water, $1 \times 30$ ml saturated NaCl, and dried quickly over sodium sulfate. TLC (Whatman K5F, 20% ethyl acetate: $CH_2Cl_2$) shows the absence of starting material on a single low Rf product. The solvent is stripped and the residue recrystallized from $CH_3CN$ to provide the naphthol in good yield.

3-(2'-Spiroadamantane)-4-methoxy-4-(5''-acetoxy)-naphth-2'-yl-1,2-dioxetane. By proceeding from this point on in the synthesis in the manner described in Example I above, i.e., acetylating methoxy-(5-hydroxynaphth-2'-yl)methylene adamantane with acetic anhydride/pyridine to give methoxy-(5-acetoxynaphth-2'-yl)methylene adamantane, and then photooxygenating this compound's ethylenic double bond, 3-(2'-spiroadamantane)-4-methoxy-4-(5''-acetoxy)naphth-2'-yl-1,2-dioxetane is obtained.

3-(2'-Spiroadamantane)-4-methoxy-4-(5''-phosphoryloxy)naohth-2'-yl-1,2-dioxetane. Phosphorylation of methoxy-(5-hydroxynaphth-2'-yl)methylene adamantane via the 2-chloro-2-oxo-1,3-dioxa phospholane method described in the aforementioned copending Edwards application to give methoxy-(5-phosphoryloxynaphth-2'-yl)methylene adamantane, and then photooxygenating this compound's ethylenic double bond, gives 3-(2'-spiroadamantane)-4-methoxy-4-(5''-phosphoryloxy)naphth-2'-yl-1,2-dioxetane.

EXAMPLE III

A dual channel assay for Human Chorionic Gonadotropins (β-chain), β-HCG, and Human Luteinizing Hormones, HLH, is carried out as follows:

Materials:

A round nylon membrane (approximately 1 inch in diameter) containing two sets of covalently immobilized capture monoclonal antibodies is used, one set for β-HCG available from Medix Biotech, Anti HCG, Cat. No. H298-01, and the second for HLH also available from Medix Biotech, Anti LH, Cat. No. L461-09. This nylon membrane is stored in a foil pouch until used.

Mouse monoclonal anti β-HCG available from Medix Biotech, Cat. No. H298-12, is conjugated with alkaline phosphatase using the glutaraldehyde coupling procedure [Voller, A., et. al., *Bull, World Health Org.,* 53, 55 (1976)] and is used as a detection antibody for β-HCG.

Mouse monoclonal anti HLH available from Medix Biotech, Cat. No. L461-03, is conjugated to carboxylesterase also using the glutaraldehyde coupling procedure referenced above, and is used as a detection antibody for HLH.

The substrate buffer solution used contains 0.05M carbonate, 1 mM $MgCl_2$, 0.1% by weight BSA (pH=0.5), and 3-(2'-spiroadamantane)-4-methoxy-4(3'-phosphoryloxy)phenyl-1,2-dioxetane disodium salt (50 µg/ml) and 3-(2'-spiroadamantane)-4-methoxy-4-(7''-acetoxy)naphth-2'-yl-1,2-dioxetane (50 µg/ml) as the chemiluminescent substrates.

The wash buffer used contains 0.05M carbonate, 1 mM $MgCl_2$ and 2% by weight BSA (pH=9.5).

Assay Procedure:

Five drops of a previously collected urine sample are placed onto the center of the assay membrane and allowed to soak into the membrane. Next, five drops of a solution containing β-HCG and HLH conjugated detection antibodies at a concentration of 0.01 millimolar are added to the assay membrane. The liquid is allowed to soak in for at least one minute. Six drops of the wash buffer are slowly added and allowed to soak in and drain for 30 to 60 seconds. Then, five drops of the buffer solution containing chemiluminescent substrates are added and allowed to soak in for approximately one minute.

The assay membrane is placed in a camera luminometer device equipped with pre-exposed calibration scales for β-HCG and LH.

The chemiluminescent light emission, generated as a function of the enzymes, alkaline phosphatase and carboxyl esterase, is imaged through a mask containing two narrow band pass filters (approximately 1 cm in diameter). Kodak Wratten Gelatin Filter No. 115 is used to image the green emission from the naphth-2'-yl-1,2-dioxetane substrate, and Kodak Wratten Filter No. 47B is used to isolate the blue emission from the phenyl dioxetane.

The relative levels of β-HCG and HLH present in the sample are determined by a comparison of the appropriate imaged spot brightness with relevant calibration scales.

EXAMPLE IV

A three-channel analysis for Herpes Simplex Virus, (HSV), Cytomegalovirus, (CMV), and Human Papiloma Virus, (HPV) is carried out as follows:

Materials:

"Gene Screen Plus", a positively charged nylon membrane (Dupont NEN Products) is used for hybridization.

The following buffers are used for the assay:

| HSV DNA PROBE ASSAY | |
|---|---|
| Materials and Buffers: | |
| Membrane: | Gene Screen Plus membrane. |
| Buffers: | Denaturation Buffer, 0.5 M NaOH |
| | Neutralization Buffer, 0.4 M $NaH_2PO_4$ (pH = 2.0) |
| | Loading Buffer, 1 part Denaturation Buffer |
| | 1 part Neutralization Buffer |
| Membrane Wetting Buffer 0.4 M Tris (pH = 7.5) | |
| Membrane Prehybridization Buffer: | |
| Substance | Final Concentration |
| 0.5 ml 100 = Denhardt's solution | 5 × |

HSV DNA PROBE ASSAY (continued)

| | |
|---|---|
| 0.5 ml 10% SDS | 0.5% |
| 2.5 ML 20 × SSPE | 5 × |
| 2.0 mg denatured, sonicated salmon sperm DNA | 200 μg/ml |
| ddH₂O | |
| 10 ml | |

Membrane Hybridization Buffer:

| Substance | Final Concentration |
|---|---|
| 0.5 ml 100 × Denhardt's solution | 5 × |
| 0.5 ml 10% SDS | 0.5% |
| 2.5 ml 20 × SSPE | 5 × |
| 2.0 mg salmon sperm DNA | 200 μg/ml |
| 2.0 ml 50% Dextran sulfate | 10% |
| — ddH₂O | |
| 10 ml | |

Wash Buffer I:
1 × SSPE/0.1% SDS
20 ml 20 × SSPE
4 ml 10% SDS
376 ml ddH₂O
400 ml

Wash Buffer II:
0.1 × SSPE/0.1% SDS preheated to wash temperature indicated on Technical Data Sheet.
2 ml 20 × SSPE
4 ml 20% SDS
394 ml ddh₂O
400 ml (heated)

Wash Buffer III:
0.1 × SSPE/0.1% SDS
2 ml 20 × SSPE
4 ml 10% SDS
394 ml ddH$_O$
400 ml

Wash Buffer IV:
3 mM Tris-HCl (pH 9.5)
0.6 ml 1 M Trizma Base
199.4 ml ddH₂O
200.0 ml

Wash Buffer V:
0.1 M Trizma HCl pH 6.0
100 × Denhart's solution

Preparation of 100 X Denhart's solution (for 100 mls):

Polyvinylpyrrolidone (2 g; mol. wt. 40K; PVP-40) and 2 g ficoll are dissolved at a temperature greater than 65° C. but less than boiling. The solution is cooled to approximately 40° C., 2 g BSA are added and the solution is brought up to the final volume of 100 ml with ddH₂O, aliquoted and stored at −20° C. BSA is easily denatured and in combination with PVP and ficoll it will not go into solution at all if it is not cooled down to −40° C. Hence, the solution is not heated over 40° C. when thawing for use.

Preparation of 20 X SSC solution:

| 20 × SSC (for 100 ml) | |
|---|---|
| 3.0 M Sodium Chloride | 17.4 g |
| 0.3 M Sodium Citrate | 8.8 g |

The volume is brought to 100 ml and the solution filtered through a 0.45 μm nitrocellulose filter and stored at room temperature.

Preparation of 20 X SSPE solution:

| 20 × SSPE pH 7.4 (for 1 liter) |
|---|
| 3.6 M NaCl |
| 200 mM Sodium phosphate 23 g dibasic, 5.92 g monobasic |
| 20 mM EDTA 7.44 g |

These materials are dissolved and adjusted to a pH of 7.4 with 5N NaOH. The volume is then brought to 1 liter and the solution filtered through a 0.45 μm nitrocellulose filter.

| 1 × TE: | |
|---|---|
| 1 × TE buffer | 10 mM Tris (pH 7.) |
| | 1 mM EDTA |
| | Autoclave |

The substrate buffer solution used contains 0.05M carbonate, 1 mM MgCl₂, 0.1% by weight BSA (Ph=9.5), and 3-(2'-spiroadamantane)-4-methoxy-4-(3'-phosphoryloxy)phenyl-1,2-dioxethane disodium salt (50 mg/ml), 3-(2'-spiroadamantane)-4-methoxy-4-(7''-acetoxy)naphth-2'-yl-1,2-dioxetane (50 mg/ml) and 3-(2'-spiroadamantane)-4-methoxy-4-(5''-β-galactosyloxy)naphth-2'-yl-1,2-dioxetane (50 mg/ml) as the chemiluminescent substrates.

Assay Procedure:

Samples (50 μl) containing DNA are denatured by incubation for 10 minutes at room temperature in 200 μl of Denaturation Buffer. Ice cold Neutralization Buffer (250 μl) is then added, and the samples placed on ice.

Nylon membrane is soaked for 15 minutes in Wetting Buffer and then inserted into a vacuum manifold device producing 2 cm diameter spots. Loading Buffer, (200 μl) is then aspirated through each well. The denatured DNA samples are then added to each well and aspirated through the membrane. The manifold is then disassembled and the DNA fixed to the membrane using a UV Transilluminator for 5 minutes. The membrane is then incubated in Prehybridization Buffer at 70° C. for 1 hour.

Dots of membrane from the region in which the sample DNA is applied are punched out and inserted into tubes for the remaining steps of the assay. The following enzyme labeled probes are used: probe for HSV labeled with alkaline phosphatase; probe for HPV labeled with β-galactosidase; probe for CMV labeled with carboxylesterase.

The enzyme labeled probes (50 ng of each probe in 200 μl of Hybridization Buffer per tube) are added to each tube and incubated for 2 hours at 70° C. The Hybridization Buffer is then removed and 400 μl of Wash Buffer I added. The tubes are then agitated for 10 minutes at room temperature. Washing is continued by first washing with 400 μl of Wash Buffer II at 50° C. for 30 minutes; then with 400 μl of Wash Buffer III at room temperature for 10 minutes; and then with 200 μl of Wash Buffer IV at room temperature.

The membrane is subsequently rinsed with Wash Buffer V at pH 6.0 and place on a piece of transparent Mylar polyester film. Then, 200 μl of the Substrate Buffer is added and allowed to soak in.

The assay membrane is placed in a camera luminometer device equipped with pre-exposed calibration scales for HSV, HPV and CMV.

The chemiluminescent light emission generated as a function of the enzymes—alkaline phosphatase, carboxyl esterase and β-galactosidase—is imaged through a mask containing three narrow bandpass filters (approximately 1 cm in diameter). Kodak Wratten Gelatin Filter No. 15 is used to image green emission from the naphthyl acetate dioxetane substrate, Kodak Wratten Filter No. 47B is used to isolate blue emission from the phenyl phosphate dioxetane, and Kodak Wratten Gelatin Filter No. 24 is used to image the orange emission from the naphthyl galactose dioxetane.

The relative levels of HSV, HPV and CMV present in the sample are determined by a comparison of the appropriate image brightness with relevant calibration scales.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

We claim:

1. An enzymatically cleavable chemiluminescent 1,2-dioxetane compound having the formula:

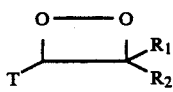

wherein $R_1$ is hydrogen, or a bond when $R_2$ is a substituent bound to the dioxetane ring through a spiro linkage, or an organic substituent that does not interfere with the production of light but satisfies the valence of the dioxetane ring carbon atom to which it is attached; $R_2$ is a fused polycyclic ring-containing fluorophore moiety bound to the dioxetane ring through a single bond or a spiro linkage and having an enzymatically cleavable labile ring substituent containing a bond which, when cleaved, renders the polycyclic moiety electron-rich to in turn render the dioxetane compound decompasable to emit light, the enzymatically cleavable labile ring substituent's point of attachment to the fused polycyclic moiety, in relation to the fused polycyclic moiety's point of attachment to the dioxetane ring, being such that the total number of ring atoms separating these points of attachment, including the ring atoms at these points of attachment, is an odd whole number; and T is a stabilizing group that prevents the dioxetane compound from decomposing before the enzymatically cleavable labile ring substituent's bond is cleaved.

2. An enzymatically cleavable chemiluminescent 1,2-dioxetane compound as recited in claim 1 in which the odd whole number is 5 or greater.

3. An enzymatically cleavable chemiluminescent 1,2-dioxetane compound as recited in claim 2 in which the fused polycyclic moiety is the residue of a fused polycyclic aromatic hydrocarbon ring fluorophoric compound containing from 9 to about 30 ring carbon atoms, inclusive.

4. An enzymatically cleavable chemiluminescent 1,2-dioxetane compound as recited in claim 3 in which the residue of a fused polycyclic aromatic hydrocarbon ring fluorophoric compound is a naphthalene residue.

5. An enzymatically cleavable chemiluminescent 1,2-dioxetane compound as recited in claim 3 in which the residue of a fused polycyclic aromatic hydrocarbon ring fluorophoric compound is an anthracene residue.

6. An enzymatically cleavable chemiulminescent 1,2-dioxetane compound as recited in claim 2 in which the fused polycyclic moiety is the residue of a less than fully aromatic fused polycyclic hydrocarbon ring fluorophoric compound containing from 10 to about 30 carbon atoms, inclusive.

7. An enzymatically cleavable chemiluminescent 1,2-dioxetane compound as recited in claim 6 in which the residue of a less than fully aromatic fused polycyclic hydrocarbon ring fluorophoric compound is a fluorene residue.

8. An enzymatically cleavable chemiluminescent 1,2-dioxetane compound as recited in claim 2 in which the fused polycyclic moiety is the residue of a fused polycyclic heterocyclic ring fluorophoric compound containing from 9 to about 30 ring atoms, inclusive.

9. An enzymatically cleavable chemiluminescent 1,2-dioxetane compound as recited in claim 8 in which the residue of a fused polycyclic heterocyclic ring fluorophoric compound is a quinoline residue.

10. An enzymatically cleavable chemiluminescent 1,2-dioxetane compound as recited in any one of claims 3–9, inclusive, in which $R_1$ is a methoxy group, $R_2$ is bound to the dioxetane ring through a single bond and T is an adamant-2-ylidene group.

11. An enzymatically cleavable 1,2-dioxetane compound as recited in claim 10 in which the enzymatically cleavable labile ring substituent is a phosphate ester group.

12. An enzymatically cleavable 1,2-dioxetane compound as recited in claim 10 in which the enzymatically cleavable labile ring substituent is a galactoside group.

13. A 3-(2'-spiroadamantane)-4-methoxy-4-(6''-phosphoryloxy)naphth-1'-yl-1,2-dioxetane salt.

14. A 3-(2'-spiroadamantane)-4-methoxy-4-(7''-phosphoryloxy)naphth-2'-yl-1,2-dioxetane salt.

15. A 3-(2'-spiroadamantane)-4-methoxy-4-(8''-phosphoryloxy)naphth-1'-yl-1,2-dioxetane salt.

16. A 3-(2'-spiroadamantane)-4-methoxy-4-(5''-phosphoryloxy)naphth-2'-yl-1,2-dioxetane salt.

17. The disodium salt of a 1,2-dioxetane compound as in any one of claims 13-16, inclusive.

18. 3-(2,-spiroadamantane)-4-methoxy-4-(5''-β-galactosyloxy)naphth-2'-yl-1,2-dioxetane.

* * * * *